United States Patent [19]

Drago et al.

[11] Patent Number: 5,274,139

[45] Date of Patent: Dec. 28, 1993

[54] METHOD FOR EFFECTIVE REACTION BETWEEN OXYGEN AND ORGANIC SUBSTANCE UTILIZING REGENERABLE HYDROPERIOXIDE OXIDANT

[75] Inventors: Russell S. Drago; Douglas E. Patton, both of Gainesville, Fla.

[73] Assignee: University of Florida, Gainesville, Fla.

[21] Appl. No.: 23,379

[22] Filed: Feb. 26, 1993

[51] Int. Cl.$^5$ .................. C07D 301/12; C07C 147/00; C07C 45/00; D21C 3/00
[52] U.S. Cl. ............................. 549/529; 162/78; 568/27; 568/28; 568/385
[58] Field of Search ..................... 568/385, 27, 28; 549/529; 162/78

[56] References Cited

U.S. PATENT DOCUMENTS

| | | | |
|---|---|---|---|
| 3,293,269 | 12/1966 | Wolgemuth | 549/529 |
| 3,449,439 | 6/1969 | Kuhnen et al. | 568/28 |
| 3,694,309 | 9/1972 | Glerer et al. | 162/78 |
| 3,707,437 | 12/1972 | Lincoln et al. | 162/78 |
| 3,719,552 | 3/1973 | Farley et al. | 162/78 |
| 3,849,499 | 11/1974 | Malievsky et al. | 568/28 |
| 4,859,799 | 8/1989 | Campestrini et al. | 568/385 |
| 5,149,880 | 9/1992 | Sawyer et al. | 568/385 |

FOREIGN PATENT DOCUMENTS 3205648 8/1983 Fed. Rep. of Germany ...... 549/529

Primary Examiner—Joseph E. Evans
Attorney, Agent, or Firm—Kerkam, Stowell, Kondracki & Clarke

[57] ABSTRACT

A method of effecting a reaction between oxygen and an organic substance comprising the stages of:

a. forming a reaction mixture comprising an N-alkylpyrrolidinone, at least one organic substance capable of reaction with oxygen and a hydroperoxide decomposition catalytically effective amount of a transition metal oxidation catalyst under a partial pressure of oxygen of at least about 16 psig, the molar ratio of organic substance to N-alkylpyrrolidinone being at least about 1:100;

b. subjecting the reaction mixture to conditions such that an oxidation reaction occurs, whereby:
  (1) at least a portion of the N-alkylpyrrolidinone is oxidized, in situ, to the corresponding hydroperoxide;
  (2) the hydroperoxide is subsequently decomposed by the catalytic action of the transition metal oxidation catalyst to the corresponding N-alkylsuccinimide, the decomposition resulting in the production of active oxygen which reacts with the organic substance;

c. after separating the reaction product of oxygen and the organic substance, contacting the product of stage b with hydrogen and a catalytically effective amount of a hydrogenation catalyst for a time and under reaction conditions effective to hydrogenate the N-alkylsuccinimide to form the corresponding N-alkylpyrrolidinone; and d. recycling the N-alkylpyrrolidinone produced in stage c to stage a.

4 Claims, No Drawings

METHOD FOR EFFECTIVE REACTION BETWEEN OXYGEN AND ORGANIC SUBSTANCE UTILIZING REGENERABLE HYDROPERIOXIDE OXIDANT

BACKGROUND OF THE INVENTION

Research leading to the completion of the invention was supported, in part, by Contract No. 160639012 awarded by the U.S. Army CRDEC. The United States Government has certain rights to the invention described and claimed herein.

FIELD OF THE INVENTION

The present invention relates to novel catalytic methods for reacting organic substances with oxygen employing regenerable alkyl hydroperoxides.

DISCUSSION OF THE PRIOR ART

A variety of catalytic systems for the oxidation of organic substances have been proposed. Many of these systems and methods involve the use of peroxidic oxidants such as organic hydroperoxides, peroxycarboxylic acids. etc., and catalysts. See, for example, the methods described in U.S. Pat. Nos. 3,350,422; 3,642,833; 3,849,451; 3,862,961 and 4,157,346 which relate to the epoxidation of olefins. In J. Am. Chem. Soc., Vol. 112, pp. 215-218 (1990), Drago et al suggested that metal-catalyzed oxidations of alkenes to epoxides proceeded in N-methylpyrrolidinone.

All of these prior art methods suffer from one or more disadvantages. Thus, most of these methods require the utilization of a separate solvent for the organic substance and peroxidic reactants. The necessity for separating the solvent from the product mixture adds to the expense of the method and detracts from the efficiency thereof.

Moreover, the peroxidic oxidant is generally consumed by the oxidation reaction, requiring not only a continuous supply of the oxidant to the reaction zone, but also the necessity for removing the reduced oxidant from the reaction product following the oxidation reaction. Obviously, these additional steps contribute greatly to the expense and inefficiency of the prior art methods.

In addition, many of the prior art methods involve the use of catalysts which are either soluble in or homogeneous with the reaction mixture and product, requiring a still further expensive and inefficient separation step before a pure oxidized product can be produced.

It is an object of the present invention to provide an improved method for effecting reactions involving organic substances utilizing a peroxidic oxidant which avoids the above-discussed disadvantages associated with the methods of the prior art.

SUMMARY OF THE INVENTION

The foregoing and other objects are realized by the present invention, one embodiment of which comprises a method of effecting a reaction between oxygen and an organic substance comprising the stages of:

a. forming a reaction mixture comprising an N-alkylpyrrolidinone, at least one organic substance capable of reaction with oxygen and a hydroperoxide decomposition catalytically effective amount of a transition metal oxidation catalyst under a partial pressure of oxygen of at least about 16 psig, the molar ratio of organic substance to N-alkylpyrrolidinone being at least about 1:2;

b. subjecting the reaction mixture to conditions such that an oxidation reaction occurs, whereby:
1. at least a portion of the N-alkylpyrrolidinone is oxidized, in situ, to the corresponding hydroperoxide; and
2. the hydroperoxide is subsequently decomposed by the catalytic action of the transition metal oxidation catalyst to the corresponding N-alkylsuccinimide, the decomposition resulting in the formation of active oxygen which reacts with the at least one organic substance;

c. after separating the reaction product of oxygen and the organic substance, contacting the product of stage b with hydrogen and a catalytically effective amount of a hydrogenation catalyst for a time and under reaction conditions effective to hydrogenate the N-alkylsuccinimide to form the corresponding N-alkylpyrrolidinone; and d. recycling the N-alkylpyrrolidinone produced in stage c to stage a.

Additional embodiments of the invention involve adaptations of the above-described method to oxidize or bleach the organic substance or to conduct a free radical initiated reaction of the organic substance as described in more detail hereinbelow.

DETAILED DESCRIPTION OF THE INVENTION

The method of the invention provides numerous valuable advantages over presently employed oxidation systems.

First, the system of the invention requires fewer steps than the methods of the prior art, thereby decreasing the costs involved in large-scale production runs.

In addition, separation and purification steps are greatly simplified, resulting in the production of a purer product at less cost.

Moreover, the regeneration and recycling of one of the reactants, namely, the N-alkylpyrrolidinone, greatly reduces costs while increasing the efficiency of the process.

Furthermore, since the N-alkylpyrrolidinone reactant also functions as a solvent for the reaction medium, thereby eliminating the need for addition of an extraneous component to the system, the product isolation and purification steps are greatly simplified.

Finally, the utilization of insoluble or heterogeneous metal catalysts greatly facilitates their removal following completion of the reaction and facilitates the product isolation and purification steps.

For the purposes of the description of the present invention, the definitions set forth below apply to the following terms:

"Oxidation" refers to the introduction of oxygen into the molecules of the organic substance by the reaction of active oxygen produced via a hydroperoxide in situ during the reaction therewith.

"Organic substance" refers to any organic compound or substrate capable of undergoing catalytic peroxidic oxidation, i.e., reaction with active oxygen, to introduce oxygen into the molecule thereof.

"Active oxygen" refers to metal-oxo, metal-alkylperoxo or reactive organic peroxo compounds.

The phrase "hydroperoxide decomposition catalytically effective amount of a transition metal oxidation catalyst" refers to any transition metal or compound alloy or complex thereof which is effective to catalyze the decomposition of organic hydroperoxides under the conditions prevailing in the reaction mixture and the amount thereof required to effect the decomposition.

"Catalytically effective amount of a hydrogenation catalyst" refers to any catalyst which catalyzes the reduction of succinimides to pyrrolidinones and the amount thereof necessary to effect such a reduction under hydrogenation conditions.

It will further be understood by those skilled in the art that the oxygen which reacts with the "organic substance" in stage b.2. derives not only from the hydroperoxide which decomposes during this step, but also from the environment of the reaction.

It will also be understood that the method of the invention may be conducted either as a batch process or as a continuous process.

Exemplary of suitable N-alkylpyrrolidinones for use in the method of the present invention are those having the formula:

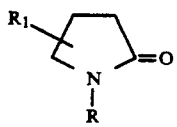

wherein R and $R_1$ may be the same or different and are alkyl groups having from 1 to about 8 carbon atoms.

The hydroperoxide corresponding to the N-alkylpyrrolidinone has the formula:

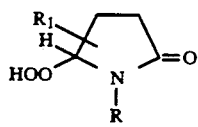

and the corresponding succinimide produced during the oxidation reaction has the formula:

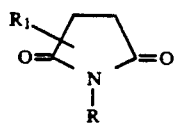

wherein R and $R_1$ have the meanings ascribed above.

The only requirements for the N-alkylpyrrolidinone reactant is that it function as a solvent for the organic substance to be oxidized; that it be capable of producing the corresponding hydroperoxide and that the latter be capable of decomposition to the corresponding succinimide while effecting the oxidation under the conditions prevailing in the oxidation stage.

Suitable N-alkylpyrrolidinones for use in the method and catalyst systems of the invention include N-methylpyrrolidinone, 1,5-dimethyl-2-pyrrolidinone, N-ethylpyrrolidinone, N-cyclohexylpyrrolidinone, 2-pyrrolidinone, etc.

Exemplary of the organic substances which may be reacted with oxygen according to the method of the present invention are alcohols, aldehydes, alkanes, alkenes, alkynes, allylic compounds, aromatic compounds, dienes, diols, ethers, nitrogen-, phosphorus- and sulfur-containing compounds, e.g., amines, phosphines, phosphonothiolates and thioethers.

According to a preferred embodiment, alkenes are readily epoxidized by the method of the present invention to produce oxiranes. Exemplary of suitable alkene starting materials are alkenes having from 2 to 16 carbon atoms, e.g., 1-hexene, cycloalkenes having from 5 to 10 carbon atoms, aralkenes having from 5 to 12 carbon atoms, e.g., trans-β-methylstyrene, allylic esters having from 5 to 15 carbon atoms, allyl alcohols having from 3 to 15 carbon atoms, terpenes, alkadienes having 5 to 20 carbon atoms, and mixtures thereof.

It will be understood by those skilled in the art, however, that any organic substance capable of reacting with oxygen or induced thereby to enter into a free radical initiated reaction, wherein the active oxygen is produced during the catalytic decomposition of hydroperoxides, may be employed in the practice of the invention.

It is preferred to employ transition metal oxidation catalysts which are insoluble in or heterogeneous with the reaction medium to facilitate their removal from the reaction product by filtration or other simple isolation procedure. Suitable such insoluble catalysts include Co-Y, Co(dmp)-Y (where dmp=2,9-dimethyl-1,10-phenanthrolene), etc.

The reaction conditions required for effecting formation of the hydroperoxide, decomposition thereof and reaction of the organic substance with oxygen are not extreme. It is necessary that the reaction be effected under oxygen at a partial pressure of at least about 16 psig, and preferably from about 16 to about 250 psig. It is preferred to employ pure oxygen; however, those skilled in the art will understand that the reaction will proceed in the presence of other gases inert to the various chemical and catalytic conversions occurring during the reaction provided that the partial pressure of oxygen is as defined above.

The molar ratio of oxygen to N-alkylpyrrolidinone need only be sufficient to ensure substantial conversion of the latter to the corresponding hydroperoxide, i.e., from about 1:100 to about 1:1.

The temperature of the reaction mixture should be sufficiently high to drive the reaction to completion within a reasonable period of time, generally from about 50° C. to about 250° C.

The molar ratio of organic substance to N-alkylpyrrolidinone is not overly critical, it only being necessary that there be sufficient N-alkylpyrrolidinone to solubilize the substance. Preferably, the molar ratio of organic substance to N-alkylpyrrolidinone should be at least about 1:100, and most preferably from about 1:2 to about 1:100.

The reduction of the succinimide by-product to the starting material, N-alkylpyrrolidinone, may be conducted under conventional hydrogenation conditions, i.e., in the presence of hydrogen and a hydrogenation catalyst such as Ru on carbon, silica gel, alumina, $CaCO_3$, zeolites, etc., wherein the molar ratio of reactant to catalyst is about 27:1.

The following non-limiting examples are provided to illustrate the invention. In the examples, the reactions were carried out in a standard Parr pressure apparatus. The reactions involved N-methylpyrrolidinone (45 ml), the appropriate catalyst ($2.3 \times 10^{-5}$ moles), the appropriate organic substance ($2.3 \times 10^{-2}$ moles), 50 psig $O_2$ pressures and most reactions were held at 75° C. in an oil bath.

The regenerations of the hydroperoxide precursor, N-methylpyrrolidinone, from the hydroperoxide decomposition product, N-methylsuccinimide, were carried out in a standard Parr pressure apparatus. The catalyst, typically 5% Ru on carbon (0.30 g), was added to an aqueous solution of N-methylsuccinimide ($4.0 \times 10^{-2}$M). The reaction conditions were generally 100 psig of hydrogen and 100° C.

EXAMPLE 1

N-methpyrrolidinone (47 ml, 47.6 g, $4.8 \times 10^{-1}$ moles) and trans-$\beta$-methylstyrene (3.0 ml, 2.73 g, $2.3 \times 10^{-2}$ moles) were placed in a 250 ml Parr pressure bottle equipped with magnetic stirring. After the pressure apparatus was assembled, the reaction was purged 3 times with $O_2$ (50 psig) and then pressurized with $O_2$ (50 psig). The reactor was placed in a 75° C. oil bath. Recharging of the reactor with $O_2$ (50 psig) was performed as needed. After 72 hours of reaction, the complete oxidation of the olefinic substrate produced benzaldehyde (33%) and 1-phenylpropylene oxide (67%).

EXAMPLE 2

In this example, the epoxidation of trans-$\beta$-methylstyrene was performed as described in Example 1 with the addition of Co(octoate)$_2$ (where octoate=2-ethylhexanoate) (0.0114 g of a 12% solution by weight of Co in mineral spirits, $2.3 \times 10^{-5}$ moles) as the metal catalyst. After 18 hours of reaction, the substrate was completely oxidized to benzaldehyde (14%) and 1-phenylpropylene oxide (86%).

EXAMPLE 3

The metal-catalyzed epoxidation of trans-$\beta$-methylstyrene was performed as described in Example 2 with the substitution of Co(OAc)$_2$. 4 H$_2$O (where OAc=acetate) (0.0058 g, $2.3 \times 10^{-5}$ moles) as the catalyst. After 16 hours of reaction, the complete oxidation of the substrate produced benzaldehyde (14%) and 1-phenylpropylene oxide (86%).

EXAMPLE 4

The metal-catalyzed epoxidation of trans-$\beta$-methylstyrene was performed as described in Example 2 with the substitution of [Ru$_3$O(pfb)$_6$(Et$_2$O)$_3$](pfb) (where pfb= perfluorobutyrate) (0.0449 g, $2.3 \times 10^{-5}$ moles) as the catalyst. After 6 hours of reaction, the complete oxidation of the substrate produced benzaldehyde (30%) and 1-phenylpropylene oxide (70%).

EXAMPLE 5

The metal-catalyzed epoxidation of trans-$\beta$-methylstyrene was performed as described in Example 2 with the substitution of Mo(O)$_2$(acac)$_2$ (where acac=acetylacetonate) (0.0076 g, $2.3 \times 10^{-5}$ moles) as the catalyst. After a reaction completion time of 48 hours, the substrate was oxidized to benzaldehyde (77%) and 1-phenylpropylene oxide (33%).

EXAMPLE 6

The metal-catalyzed epoxidation of trans-$\beta$-methylstyrene was performed as described in Example 2 with the substitution of V(O) (acac)$_2$ (where acac=acetylacetonate) (0.0062 g, $2.3 \times 10^{-5}$ moles) as the catalyst. After 26 hours of reaction, the complete oxidation of the substrate produced benzaldehyde (81%) and 1-phenylpropylene oxide (19%).

EXAMPLE 7

The metal-catalyzed epoxidation of trans-$\beta$-methylstyrene was performed as described in Example 2 with the substitution of WO$_3$ (0.0054 g, $2.3 \times 10^{-5}$ moles) as the catalyst. After 35 hours, the complete oxidation of the substrate produced benzaldehyde (64%) and 1-phenylpropylene oxide (36%).

EXAMPLE 8

The metal-catalyzed epoxidation of trans-$\beta$-methylstyrene was performed as described in Example 2 with the substitution of Mn(OAc)$_2$.4H$_2$O (where OAc=acetate) (0.0057 g, $2.32 \times 10^{-5}$ moles) as the catalyst. After 13 hours of reaction, the complete oxidation of the substrate produced benzaldehyde (74%) and 1-phenylpropylene oxide (26%).

EXAMPLE 9

The metal-catalyzed epoxidation of trans-$\beta$-methylstyrene was performed as described in Example 2 with the substitution of RuCl$_3$.3H$_2$O (0.0048 g, $2.32 \times 10^{-5}$ moles) as the catalyst. After 12 hours of reaction, the complete oxidation of the substrate produced benzaldehyde (22%) and 1-phenylpropylene oxide (78%).

EXAMPLE 10

The metal-catalyzed epoxidation of trans-$\beta$-methylstyrene was performed as described in Example 2 with the substitution of FeCl$_3$.6H$_2$O (0.0068 g, $2.32 \times 10^{-5}$ moles) as the catalyst. After 12 hours of reaction, the complete oxidation of the substrate produced benzaldehyde (20%) and 1-phenylpropylene oxide (80%).

EXAMPLE 11

The metal-catalyzed epoxidation of trans-$\beta$-methylstyrene was performed as described in Example 2 with the substitution of CoCl$_2$.6H$_2$O (0.0055 g, $2.32 \times 10^{-5}$ moles) as the catalyst. After 12 hours of reaction, the complete oxidation of the substrate produced benzaldehyde (14%) and 1-phenylpropylene oxide (86%).

EXAMPLE 12

N-methylpyrrolidinone (45 ml, 46.8 g, $4.7 \times 10^{-1}$ moles) and 1-hexene (5.0 ml, 3.37 g, $4.0 \times 10^{-2}$ moles) were placed in a 250 ml Parr pressure bottle equipped with magnetic stirring. After the pressure apparatus was assembled, the reactor was purged 3 times with $O_2$ (50 psig) and then pressurized with $O_2$ (50 psig). The reactor was placed in a 75° C. oil bath. Recharging of the reactor with $O_2$ (50 psig) was performed as needed. After a 96-hour reaction time, no oxidation products were observed.

EXAMPLE 13

In this example, the epoxidation of 1-hexene was performed as described in Example 12 with the addition of CoCl$_2$.6H$_2$O (0.0095 g, $4.0 \times 10^{-5}$ moles) as the metal catalyst. After 24 hours of reaction, the solution was found to contain 1,2-epoxyhexane (2.0%).

EXAMPLE 14

The metal-catalyzed epoxidation of 1-hexene was performed as described in Example 13 with the substitution of Co(octoate)$_2$ (where octoate=2-ethylhexanoate) (0.0024 g of a 12% solution by weight of Co in mineral spirits, $4.0 \times 10^{-5}$ moles) as the catalyst. After 24 hours of reaction, the solution contained 1,2-epoxyhexane (4.6%).

EXAMPLE 15

The metal-catalyzed epoxidation of 1-hexene was performed as described in Example 13 with the substitution of Co(hfacac)$_2$·2DMF (where hfacac=1,1,1,5,5,5-hexafluoroacetylacetonate and DMF=dimethylformamide) (0.0248 g, 4.0×10$^{-5}$ moles) as the catalyst. After 24 hours of reaction, the solution contained 1,2-epoxyhexane (2.0%).

EXAMPLE 16

The metal-catalyzed epoxidation of 1-hexene was performed as described in Example 13 with the substitution of Ti(O$^i$Pr)$_4$ (where O$^i$Pr=isopropoxide) (0.0114 g, 4.0×10$^{-5}$ moles) as the catalyst. After 48 hours, the reaction solution contained 1,2-epoxyhexane (<1%).

EXAMPLE 17

The metal-catalyzed epoxidation of 1-hexene was performed as described in Example 13 with the substitution of Mo(O)$_2$(acac)$_2$ (where acac=acetylacetonate) (0.1310 g, 4.0×10$^{-4}$ moles) as the catalyst. After 48 hours, the reaction solution contained 1,2-epoxyhexane (<1%).

EXAMPLE 18

The metal-catalyzed epoxidation of 1-hexene was performed as described in Example 17 with a reaction temperature of 100° C. After 48 hours of reaction, the solution contained 1,2-epoxyhexane (2.3%).

EXAMPLE 19

The metal-catalyzed epoxidation of 1-hexene was performed as described in Example 18 with the substitution of a "pre-generated" N-methylpyrrolidinone solution of 5-hydroperoxo-1-methyl-2-pyrrolidinone (45 ml of a 1.3M solution). After 48 hours of reaction, the solution contained 1,2-epoxyhexane (2.5%).

EXAMPLE 20

The metal-catalyzed epoxidation of 1-hexene was performed as described in Example 13 with the substitution of V(o)(acac)$_2$ (where acac=acetylacetonate) (0.1060 g, 4.0×10$^{-4}$ moles) as the catalyst. After 48 hours of reaction, the solution contained 1,2-epoxyhexane (2.2%).

EXAMPLE 21

The metal-catalyzed epoxidation of 1-hexene was performed as described in Example 13 with the substitution of RuCl$_3$·3H$_2$O (0.0083 g, 4.0×10$^{-5}$ moles) as the catalyst. After 24 hours of reaction, the solution contained 1,2-epoxyhexane (4.0%).

EXAMPLE 22

The metal-catalyzed epoxidation of 1-hexene was performed as described in Example 13 with the substitution of [Ru(dmp)$_2$(H$_2$O)$_2$][PF$_6$]$_2$ (where dmp=2,9-dimethyl-1,10-phenanthrolene) (0.3380 g, 4.0×10$^{-4}$ moles) as the catalyst and the addition of H$_2$O$_2$ (0.12 ml of a 30% aqueous solution, 1.2×10$^{-3}$ moles) to the reaction solution. After 48 hours of reaction, the solution contained 1,2-epoxyhexane (<1%).

EXAMPLE 23

The heterogeneous oxidation catalyst, Co-Y, was prepared by the following method. CoCl$_2$·6H$_2$O (4.8 g, 2.0×10$^{-2}$ moles) and distilled H$_2$O (200 ml) were placed in a 500 ml Erlenmeyer flask equipped with magnetic stirring. Na-Y (10 g, Linde LZY-52) was added to the cobalt-containing solution. The pink-colored slurry was stirred at 70° C. for 24 hours. After the cation exchange, the pink slurry was filtered and washed with distilled H$_2$O until no Cl$^-$ was present. The resulting pink solid was dried under vacuum at 150° C. for 48 hours to give a blue solid.

EXAMPLE 24

In this example, the epoxidation of 1-hexene was performed as described in Example 13 with the substitution of Co-Y (0.25 g, 4.0×10$^{-4}$ moles) as the catalyst. After 24 hours of reaction, the solution contained 1,2-epoxyhexane (4.6%).

EXAMPLE 25

The heterogeneous oxidation catalyst, Co(dmp)-Y, was prepared by the following method: 2,9-dimethyl-1,10-phenanthrolene (dmp) (7.2 g, 3.18×10$^{-2}$ moles) and ethyl alcohol (100 ml) were placed in a 250 ml Erlenmeyer flask equipped with magnetic stirring. Co-Y (5 g, 7.95×10$^{-3}$ moles) was added to the dmp solution. The resulting violet-colored slurry was stirred was stirred at room temperature for 24 hours. The violet-colored slurry was filtered and washed with 3-100 ml portions of ethyl alcohol. The violet-colored solid was dried under vacuum at room temperature for 24 hours.

EXAMPLE 26

In this example, the epoxidation of 1-hexene was performed as described in Example 13 with the substitution of Co(dmp)-Y (where dmp=2,9-dimethyl-1,10-phenanthrolene) (0.25 g, 4.0×10$^{-4}$ moles) as the catalyst. After 24 hours of reaction, the solution contained 1,2-epoxyhexane (14%).

EXAMPLE 27

N-methylsuccinimide (0.45 g, 4.0×10$^{-3}$ moles), distilled H$_2$O (100 ml) and 5% Ru on carbon (0.30 g, 1.48×10$^{-4}$ moles of Ru) were placed on a 250 ml Parr pressure bottle equipped with magnetic stirring. After the pressure apparatus was assembled, the reactor was purged 3 times with H$_2$ (100 psig) and then pressurized with H$_2$ (100 psig). The reactor was placed in a 100° C. oil bath. Recharging of the reactor with H$_2$ (100 psig) was performed as needed. After 48 hours of reaction, the reaction slurry was found to contain N-methylpyrrolidinone (>99%) and N-methylsuccinimide (<1%).

EXAMPLE 28

N-ethylpyrrolidinone (20 ml, 19.8 g, 1.8×10$^{-1}$ moles) was placed in a 250 ml Parr pressure bottle equipped with magnetic stirring. After the pressure apparatus was assembled, the reactor was purged 3 times with O$_2$ (50 psig). The reactor was placed in a 75° C. oil bath. Recharging of the reactor with O$_2$ (50 psig) was performed as needed. After 72 hours of reaction, the hydroperoxide concentration was determined by iodometric titration ([ROOH]=1.8M).

EXAMPLE 29

N-cyclohexylpyrrolidinone (20 ml, 20.1 g, $1.2 \times 10^{-1}$ moles) was reacted with $O_2$ by the procedure described in Example 28. After 72 hours of reaction, the hydroperoxide concentration was determined by iodometric titration ([ROOH]=0.18M).

EXAMPLE 30

2-Pyrrolidinone (50 ml, 56 g, $6.6 \times 10^{-1}$ moles) was reacted with $O_2$ by the procedure described in Example 28. After 72 hours of reaction, no hydroperoxide was formed.

EXAMPLE 31

2-Pyrrolidinone (50 ml, 56 g, $6.6 \times 10^{-1}$ moles) and Co-Y (0.25 g, $4.0 \times 10^{-4}$ moles) were placed in a 250 ml Parr pressure bottle equipped with magnetic stirring. After the pressure apparatus was assembled, the reactor was purged 3 times with $O_2$ (50 psig) and then pressurized with $O_2$ (50 psig). The reactor was placed in a 75° C. oil bath. Recharging of the reactor with $O_2$ (50 psig) was performed as needed. After 24 hours of reaction, the hydroperoxide concentration was determined by iodometric titration ([ROOH]=0.98M).

EXAMPLE 32

1,5-Dimethyl-2-pyrrolidinone (50 ml, 47 g, $4.1 \times 10^{-1}$ moles) was reacted with $O_2$ by the procedure described in Example 28. After 120 hours of reaction, the hydroperoxide concentration was determined by iodometric titration ([ROOH]=1.08M).

EXAMPLE 33

1,5-Dimethyl-2-pyrrolidinone (50 ml, 47 g, $4.1 \times 10^{-1}$ moles) and Co-Y (0.25 g, $4.0 \times 10^{-4}$ moles) were reacted with $O_2$ by the procedure described in Example 31. After 72 hours of reaction, the hydroperoxide concentration was determined by iodometric titration ([ROOH]=1.60M).

EXAMPLE 34

N-methylpyrrolidinone (45 ml, 46.8 g, $4.7 \times 10^{-1}$ moles) and n-butyl sulfide (5 ml, 4.19 g, $2.9 \times 10^{-2}$ moles) were placed in a 250 ml Parr pressure bottle equipped with magnetic stirring. After the pressure apparatus was assembled, the reaction was purged 3 times with $O_2$ (50 psig) and then pressurized with $O_2$ (50 psig). The reactor was placed in a 75° C. oil bath. Recharging of the reactor with $O_2$ (50 psig) was performed as needed. After 96 hours of reaction, the complete oxidation of the substrate produced sulfoxide (83%) and sulfone (17%).

EXAMPLE 35

In this example, the oxidation of n-butyl sulfide was performed as described in Example 34 with the addition of $FeSO_4 \cdot 7H_2O$ (0.0081 g, $2.9 \times 10^{-5}$ moles) as the metal catalyst. After 6 hours of reaction, the substrate was completely oxidized to sulfoxide (100%).

EXAMPLE 36

2-Propanol (50 ml, 39.1 g, $6.5 \times 10^{-1}$ moles) and N-methylpyrrolidinone (0.62 ml, 0.64 g, $6.5 \times 10^{-3}$ moles) were placed in a 250 ml Parr pressure bottle equipped with magnetic stirring. After the pressure apparatus was assembled, the reaction was purged 3 times with $O_2$ (50 psig) and then pressurized with $O_2$ (50 psig). The reactor was placed in a 100° C. oil bath. Recharging of the reactor with $O_2$ (50 psig) was performed as needed. After 120 hours of reaction, the solution was found to contain acetone (40%).

EXAMPLE 37

N-methylpyrrolidinone (50 ml, 52 g, $5.2 \times 10^{-1}$ moles) and brown paper pulp (0.25 g) were placed in a 250 ml Parr pressure bottle equipped with magnetic stirring. After the pressure apparatus was assembled, the reactor was purged 3 times with $O_2$ (50 psig) and then pressurized with $O_2$ (50 psig). The reactor was placed in a 100° C. oil bath. Recharging of the reactor with $O_2$ (50 psig) was performed as needed. After 48 hours of reaction, the reaction mixture was filtered and washed with 3-100 ml portions of distilled $H_2O$ to yield a white pulp.

EXAMPLE 38

In this example, the bleaching of brown paper pulp was performed as described in Example 37 with the addition of $CoCl_2 \cdot 6H_2O$ (0.0124 g, $5.2 \times 10^{-5}$ moles) as the metal catalyst. After 48 hours of reaction, the filtration of the reaction mixture followed by subsequent $H_2O$ washings yielded a white pulp.

We claim:

1. A method of effecting a reaction between oxygen and an organic substance comprising the stages of:
   a. forming a reaction mixture comprising an N-alkylpyrrolidinone, at least one organic substance capable of reaction with oxygen and a hydroperoxide decomposition catalytically effective amount of a transition metal oxidation catalyst under a partial pressure of oxygen of at least about 16 psig, the molar ratio of organic substance to N-alkylpyrrolidinone being at least about 1:100;
   b. subjecting said reaction mixture to conditions such that an oxidation reaction occurs, whereby:
      (1) at least a portion of said N-alkylpyrrolidinone is oxidized, in situ, to the corresponding hydroperoxide;
      (2) said hydroperoxide is subsequently by decomposed the catalytic action of said transition metal oxidation catalyst to the corresponding N-alkylsuccinimide, said decomposition resulting in the production of active oxygen which reacts with said organic substance;
   c. after separating the oxidized organic substance, contacting the product of stage b with hydrogen and a catalytically effective amount of a hydrogenation catalyst for a time and under reaction conditions effective to hydrogenate said N-alkylsuccinimide to form the corresponding N-alkylpyrrolidinone; and
   d. recycling said N-alkylpyrrolidinone produced in stage c to stage a.

2. A method according to claim 1 for oxidizing an organic substance comprising the stages of:
   a. forming a reaction mixture comprising an N-alkylpyrrolidinone, at least one organic substance capable of reaction with active oxygen and a hydroperoxide decomposition catalytically effective amount of a transition metal oxidation catalyst under a partial pressure of oxygen of at least about 16 psig, the molar ratio of organic substance to N-alkylpyrrolidinone being at least about 1:100;
   b. subjecting said reaction mixture to conditions such that an oxidation reaction occurs, whereby:

(1) at least a portion of said N-alkylpyrrolidinone is oxidized, in situ, to the corresponding hydroperoxide;
(2) said hydroperoxide is subsequently decomposed by the catalytic action of said transition metal oxidation catalyst to the corresponding N-alkylsuccinimide, thereby providing oxygen which oxidizes the organic substance to form an oxidized organic substance;

c. after separating the oxidized organic substance, contacting the product of stage b with hydrogen and a catalytically effective amount of a hydrogenation catalyst for a time and under reaction conditions effective to hydrogenate said N-alkylsuccinimide to form the corresponding N-alkylpyrrolidinone; and d. recycling said N-alkylpyrrolidinone produced in stage c to stage a.

3. A method for bleaching an organic substance by effecting a reaction between oxygen and the organic substance comprising the stages of:

a. forming a reaction mixture comprising an N-alkylpyrrolidinone, at least one organic substance capable of being bleached by reaction with oxygen and with or without a hydroperoxide decomposition catalytically effective amount of a transition metal oxidation catalyst under a partial pressure of oxygen of at least about 16 psig, the molar ratio of organic substance to N-alkylpyrrolidinone being at least about 1:100;

b. subjecting said reaction mixture to conditions such that an oxidation reaction occurs, whereby:
(1) at least a portion of said N-alkylpyrrolidinone is oxidized, in situ, to the corresponding hydroperoxide;
(2) said hydroperoxide is subsequently decomposed to the corresponding N-alkylsuccinimide, said decomposition resulting in the production of active oxygen which reacts to bleach said organic substance;

c. after separating the bleached organic substance, contacting the product of stage b with hydrogen and a catalytically effective amount of a hydrogenation catalyst for a time and under reaction conditions effective to hydrogenate said N-alkylsuccinimide to form the corresponding N-alkylpyrrolidinone; and d. recycling said N-alkylpyrrolidinone produced in stage c to stage a.

4. A method according to claim 1 for conducting a free radical initiated reaction of an organic substance comprising the stages of:

a. forming a reaction mixture comprising an N-alkylpyrrolidinone, at least one organic substance capable of undergoing a free radical initiated reaction and a hydroperoxide decomposition catalytically effective amount of a transition metal oxidation catalyst under a partial pressure of oxygen of at least about 16 psig, the molar ratio of organic substance to N-alkylpyrrolidinone being at least about 1:100;

b. subjecting said reaction mixture to conditions such that an oxidation reaction occurs, whereby:
(1) at least a portion of said N-alkylpyrrolidinone is oxidized, in situ, to the corresponding hydroperoxide which initiates the free radical initiated reaction;
(2) said hydroperoxide is subsequently decomposed by the catalytic action of said transition metal oxidation catalyst to the corresponding N-alkylsuccinimide, said decomposition resulting in the production of active oxygen which acts to initiate said free radical initiated reaction;

c. after separating the reacted organic substance, contacting the product of stage b with hydrogen and a catalytically effective amount of a hydrogenation catalyst for a time and under reaction conditions effective to hydrogenate said N-alkylsuccinimide to form the corresponding N-alkylpyrrolidinone; and d. recycling said N-alkylpyrrolidinone produced in stage c to stage a.

* * * * *

UNITED STATES PATENT AND TRADEMARK OFFICE
CERTIFICATE OF CORRECTION

PATENT NO. : 5,274,139
DATED : December 28, 1993
INVENTOR(S) : Russell S. Drago, et. al.

It is certified that error appears in the above-indentified patent and that said Letters Patent is hereby corrected as shown below:

On the Title page, item [54] in the title of the invention, line 4, change "HYDROPERIOXIDE" to -- HYDROPEROXIDE--.

Column 10, lines 42-43, claim 1, change "by decomposed" to -- decomposed by --.

Signed and Sealed this

Seventeenth Day of May, 1994

BRUCE LEHMAN

Attest:

Attesting Officer

Commissioner of Patents and Trademarks